(12) United States Patent
Glick et al.

(10) Patent No.: US 8,425,597 B2
(45) Date of Patent: Apr. 23, 2013

(54) ACCOMMODATING INTRAOCULAR LENSES

(75) Inventors: Robert E Glick, Lake Forest, CA (US); Daniel G Brady, San Juan Capistrano, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 39 days.

(21) Appl. No.: 12/617,417

(22) Filed: Nov. 12, 2009

(65) Prior Publication Data

US 2010/0057203 A1    Mar. 4, 2010

Related U.S. Application Data

(63) Continuation of application No. 11/329,276, filed on Jan. 9, 2006, which is a continuation of application No. 10/234,801, filed on Sep. 4, 2002, now abandoned, which is a continuation-in-part of application No. 09/390,380, filed on Sep. 3, 1999, now Pat. No. 6,616,692.

(60) Provisional application No. 60/132,085, filed on Apr. 30, 1999.

(51) Int. Cl.
*A61F 2/16* (2006.01)

(52) U.S. Cl.
USPC .......................................... 623/6.34; 623/6.37

(58) Field of Classification Search .................. 623/6.34
See application file for complete search history.

(56) References Cited

U.S. PATENT DOCUMENTS

| | | | |
|---|---|---|---|
| 1,483,509 | A | 2/1924 | Bugbee |
| 2,129,305 | A | 9/1938 | Feeinbloom |
| 2,274,142 | A | 2/1942 | Houchin |
| 2,405,989 | A | 6/1946 | Beach |
| 2,511,517 | A | 6/1950 | Spiegel |
| 2,834,023 | A | 5/1958 | Lieb |
| 3,004,470 | A | 10/1961 | Hans |
| 3,031,927 | A | 5/1962 | Wesley |
| 3,034,403 | A | 5/1962 | Neefe |
| RE25,286 | E | 11/1962 | de Carte |

(Continued)

FOREIGN PATENT DOCUMENTS

| | | |
|---|---|---|
| CH | 681687 A5 | 5/1993 |
| EP | 64812 A2 | 11/1982 |

(Continued)

OTHER PUBLICATIONS

English translation of Hara et al., JP 2-126847 A (May 15, 1990).*

(Continued)

*Primary Examiner* — David H. Willse
(74) *Attorney, Agent, or Firm* — Abbott Medical Optics Inc.

(57) ABSTRACT

Intraocular lenses for providing accommodation include an anterior optic, a posterior optic, and a lens structure. In one such lens, the lens structure comprises an anterior element coupled to the anterior optic and a posterior element coupled to the posterior optic. The anterior and posterior elements are coupled to one another at a peripheral region of the intraocular lens. The intraocular lens may also includes a projection extending anteriorly from the posterior element that limits posterior motion of the anterior optic so as to maintain a minimum separation between anterior optic and an anterior surface of the posterior optic.

5 Claims, 3 Drawing Sheets

U.S. PATENT DOCUMENTS

| | | |
|---|---|---|
| 3,210,894 A | 10/1965 | Bentley et al. |
| 3,227,507 A | 1/1966 | Feinbloom |
| 3,339,997 A | 9/1967 | Wesley |
| 3,420,006 A | 1/1969 | Barnett |
| 3,431,327 A | 3/1969 | Tsuetaki |
| 3,482,906 A | 12/1969 | Volk |
| 3,542,461 A | 11/1970 | Girard et al. |
| 3,673,616 A | 7/1972 | Fedorov et al. |
| 3,693,301 A | 9/1972 | Lemaltre |
| 3,711,870 A | 1/1973 | Deitrick |
| 3,718,870 A | 2/1973 | Keller |
| 3,794,414 A | 2/1974 | Wesley |
| 3,866,249 A | 2/1975 | Flom |
| 3,906,551 A | 9/1975 | Otter |
| 3,913,148 A | 10/1975 | Potthast |
| 3,922,728 A | 12/1975 | Krasnov |
| 3,925,825 A | 12/1975 | Richards et al. |
| 3,932,148 A | 1/1976 | Krewalk, Sr. |
| 3,996,626 A | 12/1976 | Richards et al. |
| 4,010,496 A | 3/1977 | Neefe |
| 4,014,049 A | 3/1977 | Richards et al. |
| 4,038,088 A | 7/1977 | White et al. |
| 4,041,552 A | 8/1977 | Ganias |
| 4,055,378 A | 10/1977 | Feneberg et al. |
| 4,056,855 A | 11/1977 | Kelman |
| 4,062,629 A | 12/1977 | Winthrop |
| 4,073,579 A | 2/1978 | Deeg et al. |
| 4,074,368 A | 2/1978 | Levy, Jr. et al. |
| 4,087,866 A | 5/1978 | Choyce et al. |
| 4,110,848 A | 9/1978 | Jensen |
| 4,159,546 A | 7/1979 | Shearing |
| 4,162,122 A | 7/1979 | Cohen |
| 4,195,919 A | 4/1980 | Shelton |
| 4,199,231 A | 4/1980 | Evans |
| 4,210,391 A | 7/1980 | Cohen |
| 4,240,719 A | 12/1980 | Gullino et al. |
| 4,244,060 A | 1/1981 | Hoffer |
| 4,244,597 A | 1/1981 | Dandl |
| 4,251,887 A | 2/1981 | Anis |
| 4,253,199 A | 3/1981 | Banko |
| 4,254,509 A | 3/1981 | Tennant |
| 4,261,065 A | 4/1981 | Tennant |
| 4,274,717 A | 6/1981 | Davenport |
| 4,285,072 A | 8/1981 | Morcher et al. |
| 4,298,994 A | 11/1981 | Clayman |
| 4,307,945 A | 12/1981 | Kitchen et al. |
| 4,315,336 A | 2/1982 | Poler |
| 4,315,673 A | 2/1982 | Guilino et al. |
| 4,316,293 A | 2/1982 | Bayers |
| 4,338,005 A | 7/1982 | Cohen |
| 4,340,283 A | 7/1982 | Cohen |
| 4,340,979 A | 7/1982 | Kelman |
| 4,361,913 A | 12/1982 | Streck |
| 4,370,760 A | 2/1983 | Kelman |
| 4,373,218 A | 2/1983 | Schachar |
| 4,377,329 A | 3/1983 | Poler |
| 4,377,873 A | 3/1983 | Reichert, Jr. |
| 4,402,579 A | 9/1983 | Poler |
| 4,404,694 A | 9/1983 | Kelman |
| 4,409,691 A | 10/1983 | Levy |
| 4,418,991 A | 12/1983 | Breger |
| 4,424,597 A | 1/1984 | Schlegel |
| 4,442,553 A | 4/1984 | Hessburg |
| 4,463,458 A | 8/1984 | Seidner |
| 4,476,591 A | 10/1984 | Arnott |
| 4,503,953 A | 3/1985 | Majewski |
| 4,504,981 A | 3/1985 | Walman |
| 4,504,982 A | 3/1985 | Burk |
| 4,512,040 A | 4/1985 | McClure |
| 4,551,864 A | 11/1985 | Akhavi |
| 4,560,383 A | 12/1985 | Leiske |
| 4,562,600 A | 1/1986 | Ginsberg et al. |
| 4,573,775 A | 3/1986 | Bayshort |
| 4,573,998 A | 3/1986 | Mazzocco |
| 4,575,878 A | 3/1986 | Dubroff |
| 4,580,882 A | 4/1986 | Nuchman et al. |
| 4,581,033 A | 4/1986 | Callahan |
| 4,596,578 A | 6/1986 | Kelman |
| 4,615,701 A | 10/1986 | Woods |
| 4,617,023 A | 10/1986 | Peyman |
| 4,618,228 A | 10/1986 | Baron et al. |
| 4,618,229 A | 10/1986 | Jacobstein et al. |
| 4,629,460 A | 12/1986 | Dyer |
| 4,636,049 A | 1/1987 | Blaker |
| 4,636,211 A | 1/1987 | Nielsen et al. |
| 4,637,697 A | 1/1987 | Freeman |
| 4,641,934 A | 2/1987 | Freeman |
| 4,661,108 A | 4/1987 | Grendahl et al. |
| 4,664,666 A | 5/1987 | Barrett |
| 4,676,792 A | 6/1987 | Praeger |
| 4,687,484 A | 8/1987 | Kaplan |
| 4,693,572 A | 9/1987 | Tsuetaki et al. |
| 4,693,716 A | 9/1987 | MacKool |
| RE32,525 E | 10/1987 | Pannu |
| 4,702,244 A | 10/1987 | Massocco |
| 4,704,016 A | 11/1987 | de Carle |
| 4,710,194 A | 12/1987 | Kelman |
| 4,720,286 A | 1/1988 | Bailey et al. |
| 4,725,278 A | 2/1988 | Shearing |
| 4,731,078 A | 3/1988 | Stoy et al. |
| 4,737,322 A | 4/1988 | Bruns et al. |
| 4,752,123 A | 6/1988 | Blaker |
| 4,759,762 A | 7/1988 | Grendahl |
| 4,769,033 A | 9/1988 | Nordan |
| 4,769,035 A | 9/1988 | Kelman |
| 4,787,903 A | 11/1988 | Grendahl |
| 4,790,847 A | 12/1988 | Woods |
| 4,813,955 A | 3/1989 | Achatz et al. |
| 4,816,031 A | 3/1989 | Pfoff |
| 4,816,032 A | 3/1989 | Hetland |
| 4,830,481 A | 5/1989 | Futhey et al. |
| 4,840,627 A | 6/1989 | Blumenthal |
| 4,842,601 A | 6/1989 | Smith |
| 4,878,910 A | 11/1989 | Koziol et al. |
| 4,878,911 A | 11/1989 | Anis |
| 4,881,804 A | 11/1989 | Cohen |
| 4,888,012 A | 12/1989 | Horn et al. |
| 4,888,015 A | 12/1989 | Domino |
| 4,888,016 A | 12/1989 | Langerman |
| 4,890,912 A | 1/1990 | Visser |
| 4,890,913 A | 1/1990 | de Carle |
| 4,892,543 A | 1/1990 | Turley |
| 4,898,461 A | 2/1990 | Portney |
| 4,906,246 A | 3/1990 | Grendahl |
| 4,917,681 A | 4/1990 | Nordan |
| 4,919,663 A | 4/1990 | Grendahl |
| 4,921,496 A | 5/1990 | Grendahl |
| 4,923,296 A | 5/1990 | Erickson |
| 4,932,966 A | 6/1990 | Christie et al. |
| 4,932,968 A | 6/1990 | Caldwell et al. |
| 4,938,583 A | 7/1990 | Miller |
| 4,946,469 A | 8/1990 | Sarfarazi |
| 4,955,902 A | 9/1990 | Kelman |
| 4,963,148 A | 10/1990 | Sulc et al. |
| 4,976,534 A | 12/1990 | Miege et al. |
| 4,976,732 A | 12/1990 | Vorosmarthy |
| 4,990,159 A | 2/1991 | Kraff |
| 4,994,058 A | 2/1991 | Raven et al. |
| 4,994,082 A | 2/1991 | Richards et al. |
| 4,994,083 A | 2/1991 | Sule et al. |
| 5,000,559 A | 3/1991 | Takahashi et al. |
| 5,002,382 A | 3/1991 | Seidner |
| 5,019,098 A | 5/1991 | Mercier |
| 5,019,099 A | 5/1991 | Nordan |
| 5,047,051 A | 9/1991 | Cumming |
| 5,047,052 A | 9/1991 | Dubroff |
| 5,071,432 A | 12/1991 | Baikoff |
| 5,089,024 A | 2/1992 | Christie et al. |
| 5,096,285 A | 3/1992 | Silberman |
| 5,108,429 A | 4/1992 | Wiley |
| 5,112,351 A | 5/1992 | Christie et al. |
| 5,129,718 A | 7/1992 | Futhey et al. |
| 5,147,397 A | 9/1992 | Christie et al. |
| 5,152,788 A | 10/1992 | Isaacson et al. |
| 5,152,789 A | 10/1992 | Willis |
| 5,158,572 A | 10/1992 | Nielsen |
| 5,166,711 A | 11/1992 | Portney |

| | | |
|---|---|---|
| 5,166,712 A | 11/1992 | Portney |
| 5,171,266 A | 12/1992 | Wiley et al. |
| 5,172,723 A | 12/1992 | Sturgis |
| 5,173,723 A | 12/1992 | Volk |
| 5,192,317 A | 3/1993 | Kalb |
| 5,192,318 A | 3/1993 | Schneider |
| 5,201,762 A | 4/1993 | Hauber |
| 5,225,858 A | 7/1993 | Portney |
| 5,258,025 A | 11/1993 | Fedorov et al. |
| 5,260,727 A | 11/1993 | Oksman et al. |
| 5,270,744 A | 12/1993 | Portney |
| 5,275,623 A | 1/1994 | Sarfarazi |
| 5,354,335 A | 10/1994 | Lipshitz et al. |
| RE34,988 E | 7/1995 | Yang et al. |
| 5,443,506 A | 8/1995 | Garabet |
| 5,476,514 A | 12/1995 | Cumming |
| 5,480,428 A | 1/1996 | Fedorov et al. |
| 5,489,302 A | 2/1996 | Skottun |
| 5,496,366 A | 3/1996 | Cuming |
| 5,521,656 A | 5/1996 | Portney |
| 5,549,760 A | 8/1996 | Becker |
| 5,562,731 A | 10/1996 | Cumming |
| 5,574,518 A | 11/1996 | Mercure |
| 5,578,081 A | 11/1996 | McDonald |
| 5,593,436 A | 1/1997 | Langerman |
| 5,607,472 A | 3/1997 | Thompson |
| 5,628,795 A | 5/1997 | Langerman |
| 5,628,796 A | 5/1997 | Suzuki |
| 5,628,797 A | 5/1997 | Richer |
| 5,652,014 A | 7/1997 | Galin et al. |
| 5,652,638 A | 7/1997 | Roffman et al. |
| 5,657,108 A | 8/1997 | Portney |
| 5,674,282 A | 10/1997 | Cumming |
| 5,682,223 A | 10/1997 | Menezes et al. |
| 5,684,560 A | 11/1997 | Roffman et al. |
| 5,766,244 A | 6/1998 | Binder |
| 5,769,890 A | 6/1998 | McDonald |
| 5,776,191 A | 7/1998 | Mazzocco |
| 5,776,192 A | 7/1998 | McDonald |
| 5,800,533 A | 9/1998 | Eggleston et al. |
| 5,814,103 A | 9/1998 | Lipshitz et al. |
| 5,824,074 A | 10/1998 | Koch |
| 5,843,188 A | 12/1998 | McDonald |
| 5,847,802 A | 12/1998 | Menezes et al. |
| 5,876,442 A | 3/1999 | Lipshitz et al. |
| 5,898,473 A | 4/1999 | Seidner et al. |
| 5,968,094 A | 10/1999 | Werblin et al. |
| 5,984,962 A | 11/1999 | Anello et al. |
| 6,013,101 A | 1/2000 | Israel |
| 6,051,024 A | 4/2000 | Cumming |
| 6,083,261 A | 7/2000 | Callahan et al. |
| 6,096,078 A | 8/2000 | McDonald |
| 6,110,202 A | 8/2000 | Barraquer et al. |
| 6,117,171 A | 9/2000 | Skottun |
| 6,120,538 A | 9/2000 | Rizzo, III et al. |
| 6,136,026 A | 10/2000 | Israel |
| 6,152,958 A | 11/2000 | Nordan |
| 6,176,878 B1 | 1/2001 | Gwon et al. |
| 6,197,058 B1 | 3/2001 | Portney |
| 6,197,059 B1 | 3/2001 | Cumming |
| 6,200,342 B1 | 3/2001 | Tassignon |
| 6,217,612 B1 | 4/2001 | Woods |
| 6,231,603 B1 | 5/2001 | Lang et al. |
| 6,299,641 B1 | 10/2001 | Woods |
| 6,302,911 B1 | 10/2001 | Hanna |
| 6,322,589 B1 | 11/2001 | Cumming |
| 6,387,126 B1 | 5/2002 | Cumming |
| 6,399,734 B1 | 6/2002 | Hodd et al. |
| 6,406,494 B1 | 6/2002 | Lagutte et al. |
| 6,423,094 B1 | 7/2002 | Sarfarazi |
| 6,443,985 B1 | 9/2002 | Woods |
| 6,464,725 B2 | 10/2002 | Skottun |
| 6,485,516 B2 | 11/2002 | Boehm |
| 6,488,708 B2 | 12/2002 | Sarfarazi |
| 6,494,911 B2 | 12/2002 | Cumming |
| 6,503,276 B2 | 1/2003 | Lang et al. |
| 6,524,340 B2 | 2/2003 | Israel |
| 6,533,813 B1 | 3/2003 | Lin et al. |
| 6,551,354 B1 | 4/2003 | Ghazizadeh et al. |
| 6,554,859 B1 | 4/2003 | Lang et al. |
| 6,558,420 B2 | 5/2003 | Green |
| 6,592,621 B1 | 7/2003 | Domino |
| 6,599,317 B1 | 7/2003 | Weinschenk, III et al. |
| 6,616,691 B1 | 9/2003 | Tran |
| 6,616,692 B1 | 9/2003 | Glick et al. |
| 6,638,305 B2 | 10/2003 | Laguette |
| 6,638,306 B2 | 10/2003 | Cumming |
| 6,645,246 B1 | 11/2003 | Weinschenk et al. |
| 6,660,035 B1 | 12/2003 | Lang et al. |
| 6,695,881 B2 | 2/2004 | Peng et al. |
| 6,749,633 B1 | 6/2004 | Lorenzo et al. |
| 6,749,634 B2 | 6/2004 | Hanna |
| 6,761,737 B2 | 7/2004 | Zadno-Azizi et al. |
| 6,764,511 B2 | 7/2004 | Zadno-Azizi et al. |
| 6,767,363 B2 | 7/2004 | Bandhauer et al. |
| 6,786,934 B2 | 9/2004 | Zadno-Azizi et al. |
| 6,818,017 B1 | 11/2004 | Shu |
| 6,818,158 B2 | 11/2004 | Pham et al. |
| 6,846,326 B2 | 1/2005 | Zadno-Azizi et al. |
| 6,855,164 B2 | 2/2005 | Glazier |
| 6,858,040 B2 | 2/2005 | Nguyen et al. |
| 6,884,261 B2 | 4/2005 | Zadno-Azizi et al. |
| 6,884,263 B2 | 4/2005 | Valyunin et al. |
| 6,899,732 B2 | 5/2005 | Zadno-Azizi et al. |
| 6,926,736 B2 | 8/2005 | Peng et al. |
| 6,930,838 B2 | 8/2005 | Schachar |
| 7,018,409 B2 | 3/2006 | Glick et al. |
| 7,025,783 B2 | 4/2006 | Brady et al. |
| 7,041,134 B2 | 5/2006 | Nguyen et al. |
| 7,087,080 B2 | 8/2006 | Zadno-Azizi et al. |
| 7,097,660 B2 | 8/2006 | Portney |
| 7,118,596 B2 | 10/2006 | Zadno-Azizi et al. |
| 7,118,597 B2 | 10/2006 | Miller et al. |
| 7,125,422 B2 | 10/2006 | Woods et al. |
| 7,150,759 B2 | 12/2006 | Paul et al. |
| 7,179,292 B2 | 2/2007 | Worst et al. |
| 7,198,640 B2 | 4/2007 | Nguyen |
| 7,220,279 B2 | 5/2007 | Nun |
| 7,223,288 B2 | 5/2007 | Zhang et al. |
| 7,226,478 B2 | 6/2007 | Ting et al. |
| 7,238,201 B2 | 7/2007 | Portney et al. |
| 7,452,362 B2 | 11/2008 | Zadno-Azizi et al. |
| 7,452,378 B2 | 11/2008 | Zadno-Azizi et al. |
| 7,503,938 B2 | 3/2009 | Phillips |
| 7,615,056 B2 | 11/2009 | Ayton et al. |
| 7,645,300 B2 | 1/2010 | Tsai |
| 7,662,180 B2 | 2/2010 | Paul et al. |
| 7,744,603 B2 | 6/2010 | Zadno-Azizi et al. |
| 7,744,646 B2 | 6/2010 | Zadno-Azizi et al. |
| 7,815,678 B2 | 10/2010 | Ben Nun |
| 2001/0001836 A1 | 5/2001 | Cumming |
| 2002/0103536 A1 | 8/2002 | Landreville et al. |
| 2002/0107568 A1 | 8/2002 | Zadno-Azizi et al. |
| 2002/0111678 A1 | 8/2002 | Zadno-Azizi et al. |
| 2002/0116058 A1 | 8/2002 | Zadno-Azizi et al. |
| 2002/0116060 A1 | 8/2002 | Nguyen et al. |
| 2002/0120329 A1 | 8/2002 | Lang et al. |
| 2002/0161434 A1 | 10/2002 | Laguette et al. |
| 2002/0188351 A1 | 12/2002 | Laguette |
| 2002/0193876 A1 | 12/2002 | Lang et al. |
| 2003/0004569 A1 | 1/2003 | Haefliger |
| 2003/0060878 A1 | 3/2003 | Shadduck |
| 2003/0060881 A1 | 3/2003 | Glick et al. |
| 2003/0078657 A1 | 4/2003 | Zadno-Azizi et al. |
| 2003/0078658 A1 | 4/2003 | Zadno-Azizi |
| 2003/0083744 A1 | 5/2003 | Khoury |
| 2003/0109925 A1 | 6/2003 | Ghazizadeh et al. |
| 2003/0109926 A1 | 6/2003 | Portney |
| 2003/0114927 A1 | 6/2003 | Nagamoto |
| 2003/0130732 A1 | 7/2003 | Sarfarazi |
| 2003/0135272 A1 | 7/2003 | Brady et al. |
| 2003/0149480 A1 | 8/2003 | Shadduck |
| 2003/0158599 A1 | 8/2003 | Brady et al. |
| 2003/0187504 A1 | 10/2003 | Weinschenk et al. |
| 2003/0187505 A1 | 10/2003 | Liao |
| 2003/0204254 A1 | 10/2003 | Peng et al. |
| 2003/0204255 A1 | 10/2003 | Peng et al. |
| 2004/0015236 A1 | 1/2004 | Sarfarazi |

| | | | |
|---|---|---|---|
| 2004/0039446 A1 | 2/2004 | McNicholas | |
| 2004/0054408 A1 | 3/2004 | Glick et al. | |
| 2004/0082993 A1 | 4/2004 | Woods | |
| 2004/0082994 A1 | 4/2004 | Woods et al. | |
| 2004/0082995 A1 | 4/2004 | Woods | |
| 2004/0111153 A1 | 6/2004 | Woods et al. | |
| 2004/0117013 A1 | 6/2004 | Schachar | |
| 2004/0148023 A1 | 7/2004 | Shu | |
| 2004/0158322 A1 | 8/2004 | Shen | |
| 2004/0162612 A1 | 8/2004 | Portney et al. | |
| 2004/0167621 A1 | 8/2004 | Peyman | |
| 2004/0181279 A1 | 9/2004 | Nun | |
| 2004/0215340 A1 | 10/2004 | Messner et al. | |
| 2004/0230300 A1 | 11/2004 | Bandhauer et al. | |
| 2004/0249456 A1 | 12/2004 | Cumming | |
| 2005/0018504 A1 | 1/2005 | Marinelli et al. | |
| 2005/0021139 A1 | 1/2005 | Shadduck | |
| 2005/0027354 A1 | 2/2005 | Brady et al. | |
| 2005/0060032 A1 | 3/2005 | Magnante et al. | |
| 2005/0085906 A1 | 4/2005 | Hanna | |
| 2005/0085907 A1 | 4/2005 | Hanna | |
| 2005/0113914 A1 | 5/2005 | Miller et al. | |
| 2005/0125057 A1 | 6/2005 | Cumming | |
| 2005/0125058 A1 | 6/2005 | Cumming et al. | |
| 2005/0131535 A1 | 6/2005 | Woods | |
| 2005/0137703 A1 | 6/2005 | Chen | |
| 2005/0234547 A1 | 10/2005 | Nguyen et al. | |
| 2005/0267575 A1 | 12/2005 | Nguyen et al. | |
| 2005/0288785 A1 | 12/2005 | Portney et al. | |
| 2006/0064162 A1 | 3/2006 | Klima | |
| 2006/0100703 A1 | 5/2006 | Evans et al. | |
| 2006/0111776 A1 | 5/2006 | Glick et al. | |
| 2006/0116765 A1 | 6/2006 | Blake et al. | |
| 2006/0178741 A1 | 8/2006 | Zadno-Azizi et al. | |
| 2006/0184244 A1 | 8/2006 | Nguyen et al. | |
| 2006/0238702 A1 | 10/2006 | Glick et al. | |
| 2006/0259139 A1 | 11/2006 | Zadno-Azizi et al. | |
| 2006/0271187 A1 | 11/2006 | Zadno-Azizi et al. | |
| 2007/0050025 A1 | 3/2007 | Nguyen et al. | |
| 2007/0067872 A1 | 3/2007 | Mittendorf et al. | |
| 2007/0078515 A1 | 4/2007 | Brady | |
| 2007/0100444 A1 | 5/2007 | Brady et al. | |
| 2007/0106381 A1 | 5/2007 | Blake | |
| 2007/0108643 A1 | 5/2007 | Zadno-Azizi et al. | |
| 2007/0123591 A1 | 5/2007 | Kuppuswamy et al. | |
| 2007/0129798 A1 | 6/2007 | Chawdhary | |
| 2007/0135915 A1 | 6/2007 | Klima | |
| 2007/0213817 A1 | 9/2007 | Esch et al. | |
| 2007/0260309 A1 | 11/2007 | Richardson | |
| 2007/0299487 A1 | 12/2007 | Shadduck | |
| 2008/0125790 A1 | 5/2008 | Tsai et al. | |
| 2008/0161913 A1 | 7/2008 | Brady et al. | |
| 2008/0161914 A1 | 7/2008 | Brady et al. | |
| 2009/0012609 A1 | 1/2009 | Geraghty et al. | |

FOREIGN PATENT DOCUMENTS

| | | | |
|---|---|---|---|
| EP | 328117 A2 | 8/1989 | |
| EP | 331457 A2 | 9/1989 | |
| EP | 0 337 390 A2 * | 10/1989 | |
| EP | 336877 A1 | 10/1989 | |
| EP | 356050 A1 | 2/1990 | |
| EP | 420549 A2 | 4/1991 | |
| EP | 507292 A1 | 10/1992 | |
| EP | 601845 A1 | 6/1994 | |
| EP | 766540 A1 | 4/1997 | |
| EP | 766540 B1 | 8/1999 | |
| EP | 1647241 A2 | 4/2006 | |
| JP | 7222760 A2 | 8/1995 | |
| JP | 9501856 T2 | 2/1997 | |
| JP | 2003190193 A | 7/2003 | |
| RU | 2014038 C1 | 6/1994 | |
| RU | 2014039 C1 | 6/1994 | |
| WO | WO8404449 A1 | 11/1984 | |
| WO | WO9305733 A1 | 4/1993 | |
| WO | WO9503783 A1 | 2/1995 | |
| WO | WO9610968 A1 | 4/1996 | |
| WO | WO9625126 A1 | 8/1996 | |
| WO | WO9712272 A1 | 4/1997 | |
| WO | WO9727825 A1 | 8/1997 | |
| WO | WO9856315 A1 | 12/1998 | |
| WO | WO9903427 A1 | 1/1999 | |
| WO | WO0021467 A1 | 4/2000 | |
| WO | WO0027315 A1 | 5/2000 | |
| WO | WO0061036 A1 | 10/2000 | |
| WO | WO0066037 A1 | 11/2000 | |
| WO | WO0066039 A1 | 11/2000 | |
| WO | WO0066040 A1 | 11/2000 | |
| WO | WO0119288 A1 | 3/2001 | |
| WO | WO0119289 A1 | 3/2001 | |
| WO | WO0128144 A1 | 4/2001 | |
| WO | WO0134066 A1 | 5/2001 | |
| WO | WO0164136 A2 | 9/2001 | |
| WO | WO0219949 A2 | 3/2002 | |
| WO | WO02071983 A1 | 9/2002 | |
| WO | WO03015669 A1 | 2/2003 | |
| WO | WO03034949 A2 | 5/2003 | |
| WO | WO03059196 A2 | 7/2003 | |
| WO | WO03059208 A2 | 7/2003 | |
| WO | WO03075810 A1 | 9/2003 | |
| WO | WO2004000171 A1 | 12/2003 | |
| WO | WO2005018504 A1 | 3/2005 | |
| WO | WO2005084587 A | 9/2005 | |
| WO | WO2005115278 A1 | 12/2005 | |
| WO | WO2006025726 A1 | 3/2006 | |
| WO | WO2006118452 A1 | 11/2006 | |
| WO | WO2007040964 A1 | 4/2007 | |
| WO | WO2007067872 A2 | 6/2007 | |
| WO | WO2008077795 A2 | 7/2008 | |
| WO | WO2008079671 A1 | 7/2008 | |
| WO | WO2008200889 A1 | 12/2008 | |
| WO | WO2010093823 A2 | 8/2010 | |

OTHER PUBLICATIONS

Hara T., et al., "Accomodative Intraocular Lens with Spring Action Part 1 Design and Placement in an Excised Animal Eye," Opthalmic Surgery, 1990, vol. 21 (2), pp.128-133.

International Search Report and Written Opinion for Application No. PCT/US2010/023946, mailed on Feb. 22, 2011, 10 pages.

International Search Report for Application No. PCT/US00/11565, mailed on Sep. 8, 2008, 3 pages.

International Search Report for Application No. PCT/US07/72275, mailed on Sep. 9, 2008, 6 pages.

U.S. Appl. No. 09/657,325, filed Sep. 7, 2000.
U.S. Appl. No. 09/390,380, filed Sep. 3, 1999.
U.S. Appl. No. 09/522,326, filed Mar. 9, 2000.
U.S. Appl. No. 09/532,910, filed Mar. 22, 2000.
U.S. Appl. No. 09/565,036, filed May 3, 2000.
U.S. Appl. No. 09/656,661, filed Sep. 7, 2000.
U.S. Appl. No. 09/657,251, filed Sep. 7, 2000.
U.S. Appl. No. 09/795,929, filed Feb. 28, 2001.
U.S. Appl. No. 09/822,040, filed Mar. 30, 2001.

Simonov A.N., et al., "Cubic Optical Elements for an Accommodative Intraocular Lens," Optics Express, 2006, vol. 14 (17), pp. 7757-7775.

U.S. Appl. No. 10/280,918, filed Aug. 5, 2003 cited by other.
U.S. Appl. No. 10/280,937, filed Oct. 25, 2005 cited by other.
U.S. Appl. No. 09/631,223, filed Aug. 2, 2000.
U.S. Appl. No. 09/721,072, filed Nov. 20, 2000.

* cited by examiner

ACCOMMODATING INTRAOCULAR LENSES

CROSS REFERENCE TO RELATED APPLICATION

This application is a continuation application of U.S. patent application Ser. No. 11/329,276, filed on Jan. 9, 2006, which is continuation application of U.S. patent application Ser. No. 10/234,801, filed on Sep. 4, 2002, now abandoned, which is a continuation-in-part application of U.S. patent application Ser. No. 09/390,380, filed Sep. 3, 1999, now U.S. Pat. No. 6,616,692, which claims the benefit of U.S. provisional application 60/132,085, filed Apr. 30, 1999, the entire contents of each of which applications are hereby incorporated by reference in their entirety for all purposes as if fully set forth herein.

BACKGROUND OF THE INVENTION

The present invention relates to intraocular lens combinations. More particularly, the invention relates to intraocular lens combinations which are adapted to provide substantial benefits, such as accommodating movement and/or inhibition of posterior capsule opacification (PCO) in the eye.

The human eye includes an anterior chamber between the cornea and iris, a posterior chamber including a capsular bag containing a crystalline lens, a ciliary muscle, a vitreous chamber behind the lens containing the vitreous humor, and a retina at the rear of this chamber. The human eye has a natural accommodation ability. The contraction and relaxation of the ciliary muscle provides the eye with near, intermediate and distant vision. This ciliary muscle action shapes the natural crystalline lens to the appropriate optical configuration for focusing light rays entering the eye on the retina.

After the natural crystalline lens is removed, for example, because of cataract or other condition, a conventional, monofocal IOL can be placed in the posterior chamber. Such a conventional IOL has very limited, if any, accommodating ability. However, the wearer of such an IOL continues to require the ability to view both near and far (distant) objects. Corrective spectacles may be employed as a useful solution. Recently, multifocal IOLs without accommodating movement have been used to provide near/far vision correction.

Attempts have been made to provide IOLs with accommodating movement along the optical axis of the eye as an alternative to shape changing. Examples of such attempts are set forth in Levy U.S. Pat. No. 4,409,691, U.S. Pat. Nos. 5,674,282 and 5,496,366 to Cumming, U.S. Pat. No. 6,176,878 to Gwon et al, U.S. Pat. No. 6,231,603 to Lang et al, and U.S. Pat. No. 6,406,494 to Laguette et al. The disclosure of each of these patents is incorporated herein by reference.

One problem that exists with such IOLs is that they often cannot move sufficiently to obtain the desired accommodation. The degree of accommodation has been closely related to the lens prescription of the individual patient. In addition, the presence of such lenses can result in cell growth from the capsular bag onto the optics of such lenses. Such cell growth, often referred to as posterior capsule opacification (PCO), can interfere with the clarity of the optic to the detriment of the lens wearer's vision.

It would be advantageous to provide IOLs adapted for accommodating movement, which can preferably achieve an acceptable amount of accommodation and/or a reduced risk of PCO.

SUMMARY OF THE INVENTION

New intraocular lens combinations (ILCs) have been disclosed. The present ILCs provide distance, near and intermediate vision through position, preferably axial position, changes in the eye. The present combinations preferably enhance the degree of accommodation achieved in spite of the movement and space limitations within the eye. One advantage of the present ILCs is the ability to standardize the prescription or optical power of the moving or accommodating lens of the ILC. Thus, the required amount of movement in the eye to achieve accommodation can be substantially the same for all patients. This greatly facilitates the design of the moving or accommodating lens. Further, with at least certain of the present ILCs, inhibition of PCO is obtained. The present ILCs are relatively straightforward in construction, can be implanted or inserted into the eye using systems and procedures which are well known in the art and function effectively with little or no additional treatments or medications being required.

In one broad aspect of the present invention, intraocular lens combinations (ILCs) comprise a first optic body, second optic body and a movement assembly. The first optic body has a negative or plano optical power and is adapted to be placed in a substantially fixed position in a mammalian eye. In those cases where the first optic body has a negative optical power, it is also called the compensating optic body. The second optic body, also called the primary optic body, has a higher optical power than the first optic body. The movement assembly is coupled to the second optic body and is adapted to cooperate with the eye, for example, the zonules, ciliary muscle and capsular bag of the eye, to effect accommodating movement of the second optic body in the eye.

Advantageously, the second optic body has a high plus optical power to reduce the amount of movement, for example, axial movement, in the eye needed to provide accommodation for intermediate and near vision. The negative or minus optical power of the first optic body compensates for the excess plus or positive optical power in the first optic body. The use of such a compensating lens, that is the first optic body having a negative optical power, can allow for standardization of the optical power correction in the second optic body. In other words, the optical power of the second optic body, that is the primary or movable optic body, can be approximately equal from optic body to optic body, while the optical power of the first optic body, that is the compensating or fixed optic body, is adjusted from optic body to optic body to meet the specific vision correction needs (prescription) of each individual patient. Consequently, the required amount of movement of the second optic body in the eye can be approximately the same for all patients.

The present ILCs provide accommodation, preferably an acceptable degree of accommodation, in spite of movement and space limitations in the eye. For example, the maximum theoretical amount of axial movement for a simple disc lens having an overall diameter of 11 millimeters (mm) and an optic diameter of 5 mm that undergoes 1 mm of compression in its diameter is about 1.65 mm. The amount of axial movement required for a plus 15 diopter optic to provide 2.5 diopters of additional power in the spectacle plane is about 2.6 mm. However, a plus 30 diopter optic requires only 1.2 mm of axial movement to provide 2.5 diopters of additional power in the spectacle plane. Thus, by increasing the plus power of the second optic, which is adapted for accommodating movement, a reduced amount of movement is needed to achieve higher or enhanced degrees of accommodation. The first or fixed optic preferably has a minus power to compensate for the excess plus power in the second optic.

The present ILCs preferably include first and second optics with optical powers which provide a net plus optical power. To illustrate, assume that the patient requires a plus 15 diopter correction. The first optic body is provided with a minus 15 diopter optical power and the second optic body with a plus 30 diopter optical power. The net optical power of this ILC is approximately the sum of minus 15 diopters and plus 30 diopters or plus 15 diopters, the desired prescription for the patient in question. The powers of the first and second optics are only approximately additive since the net power of the combination also depends on other factors including, but not limited to, the separation of the two optics, the magnitude of the power of each individual optic body and its location in the eye and the like factors. Also, by adjusting the optical power of the first optic body, the net optical power of the ILC can be adjusted or controlled even though the optical power of the second optic body is standardized or remains the same, for example, at a plus 30 diopter optical power. By standardizing the optical power of the second optic body, the amount of movement in the eye required to obtain a given level of accommodation is substantially the same, and preferably well within the space limitations in the eye, from patient to patient.

In one very useful embodiment, the movement assembly comprises a member including a proximal end region coupled to the second optic body and a distal end region extending away from the second optic body and adapted to contact a capsular bag of the eye. Such movement assembly may completely circumscribe the second optic body or may be such as to only partially circumscribe the second optic body.

The second optic body preferably is adapted to be positioned in the capsular bag of the eye.

The first optic body may be coupled to a fixation member, or a plurality of fixation members, adapted to assist in fixating the first optic body in the eye. Each fixation member preferably has a distal end portion extending away from the first optic body. In one embodiment, the distal end portion of the fixation member is adapted to be located in the capsular bag of the eye. Alternately, the distal end portion of the fixation member may be located in contact with a sulcus of the eye. As a further alternate, the distal end portion of the fixation member may be adapted to be located in an anterior chamber of the eye.

The first optic body may be located posterior in the eye relative to the second optic body or anterior in the eye relative to the second optic body. In a useful embodiment, the first optic body is adapted to be positioned in contact with the posterior wall of the capsular bag of the eye. This positioning of the first optic body provides for effective compensation of the plus or positive vision correction power of the second optic body. In addition, by having the first optic body in contact with the posterior wall of the capsular bag, cell growth from the capsular bag onto the ILC, and in particular onto the first and second optics of the ILC, is reduced. This, in turn, reduces the risk of or inhibits posterior capsule opacification (PCO).

In one embodiment, the fixation member or members and the movement assembly are secured together, preferably permanently secured together. Thus, when inserting the ILC into the eye, a single combined structure can be inserted. This reduces the need to position the first and second optics relative to each other. Put another way, this feature allows the surgeon to very effectively and conveniently position the ILC in the eye with reduced surgical trauma to the patient.

The fixation member and movement assembly may be secured, for example, fused, together at the distal end portion of the fixation member and the distal end region of the movement assembly.

In an alternate embodiment, there is no connection between the fixation member or members of the compensating lens and the movement assembly of the primary lens. That is, the compensating lens and primary lens are completely separate from and independent of one another, enabling them to be implanted consecutively, rather than simultaneously. This allows the lenses to be inserted through a smaller incision than would be possible with a combined structure. In the case of separate lenses, however, special care must be taken to axially align the two lenses in order to avoid decentration issues.

In another broad aspect of the present invention, ILCs are provided which comprise a first optic body having a posterior surface adapted to be positioned in contact with a posterior wall of the capsular bag of the eye; a second optic body adapted to focus light toward a retina of the eye; and a movement assembly coupled to the second optic body and adapted to cooperate with the eye to effect accommodating movement of the second optic body in the eye. The first optic body has a substantially plano optical power or a negative optical power. These ILCs are particularly adapted to inhibit PCO.

The first optic body of these combinations preferably is adapted to be placed in a substantially fixed position in the eye. The posterior surface of the first optic body advantageously is configured to substantially conform to a major portion, that is, at least about 50%, of the posterior wall of the capsular bag of the eye in which the combination is placed. More preferably, the posterior surface of the first optic body is configured to substantially conform to substantially all of the posterior wall of the capsular bag. Such configuration of the first optic body is very useful in inhibiting cell growth from the eye onto the first and second optics and in inhibiting PCO.

In one embodiment, the first optic body, which contacts the posterior wall of the capsular, has a substantially plano optical power and the second optic body has a far vision correction power. In an alternate embodiment, the first optic body has a negative optical power and the second optic body has a positive optical power, more preferably, so that the optical powers of the first and second optics provide a net plus optical power in the eye in which the combination is placed. In this latter embodiment, the second, or primary, optic body is preferably placed in the capsular bag, while the first, or compensating, optic body, may be placed in the bag, the sulcus or the anterior chamber, or attached to the iris.

In a very useful embodiment, the first optic body includes an anterior surface and at least one projection extending anteriorly from this anterior surface. The at least one projection is positioned to limit the posterior movement of the second optic body in the eye. Thus, the movement of the second optic body is effectively controlled to substantially maintain the configuration of the combination and/or to substantially maintain an advantageous spacing between the first and second optics.

The movement assembly may be structured and functions similarly to movement assembly of the previously described ILCs.

The first optic body may have a fixation member or members coupled thereto. The fixation member or members are adapted to assist in fixating the first optic body in the eye, that is in contact with the posterior wall of the capsular bag of the eye. In one embodiment, the first optic body itself is configured and/or structured so that no fixation member or members are needed to maintain the first optic body in contact with the posterior wall of the capsular bag of the eye. The first optic body and the movement assembly of these ILCs may be secured together.

In general, the first and second optics of the present ILCs may be made of any suitable materials. Preferably, the first and second optics are made of polymeric materials. More preferably, the first and second optics and the movement assembly, and the fixation member(s), if any, are deformable for insertion through a small incision in the eye.

The present movement assemblies are sufficiently flexible to facilitate movement of the second optic body in the eye upon being acted upon by the eye. In one very useful embodiment, the movement assembly includes a hinge assembly, preferably adapted and positioned to facilitate the accommodating movement of the second optic body.

In those embodiments in which the first optic body has a substantially plano optic body power, the second optic body preferably has a far vision correction power, more preferably such a power for infinity, in the unaccommodated state.

In a further broad aspect of the present invention, methods for inserting an ILC in an eye are provided. Such methods comprise providing an ILC in accordance with the present invention, as described herein. The ILC is placed into the eye, for example, in the capsular bag of the eye or partly in the capsular bag of the eye, using equipment and techniques which are conventional and well known in the art. The ILC is placed in a rest position in the eye, for example, a position so that the eye, and in particular the ciliary muscle and zonules of the eye, effectively cooperate with the movement assembly to move the second optic body of the ILC anteriorly in the eye from the rest position to provide for positive accommodation. No treatments or medications, for example, to paralyze the ciliary muscle, to facilitate fibrosis or otherwise influence the position of the ILC in the eye, are required.

In one embodiment, the primary and compensating lenses are connected by the fixation member or members and the movement assembly, and are thus simultaneously implanted in the eye. In another embodiment, the primary lens is implanted first and centered about the optical axis. The the compensating lens is then inserted anteriorly of the primary lens and optically aligned with the primary lens. This latter embodiment may require a smaller incision than that required for the unitary combination of the former embodiment. In addition, this embodiment allows for refractive measurements to be made after the primary lens has been implanted, so that any new refractive errors that may have been introduced as a result of the surgery itself can be taken into account, and a more accurate prescription for the compensating lens can be obtained.

Preferably, the first and second optics and the movement assembly are deformed prior to being placed into the eye. Once the ILC is placed in the eye, and after a normal period of recovery from the surgical procedure, the ILC, in combination with the eye, provides the mammal or human wearing the ILC with effective accommodation, preferably with reduced risk of PCO. In the unaccommodated state, the ILC preferably provides the mammal or human wearing the ILC with far vision correction.

In another broad aspect of the of the present invention, an intraocular lens comprises an anterior optic, a posterior optic, and a lens structure. The lens structure comprises an anterior element coupled to the anterior optic and a posterior element coupled to the posterior optic. The anterior and posterior elements are coupled to one another at a peripheral region of the intraocular lens. The intraocular lens also includes a projection extending anteriorly from the posterior element that limits posterior motion of the anterior optic so as to maintain a minimum separation between anterior optic and an anterior surface of the posterior optic.

Any and all features described herein and combinations of such features are included within the scope of the present invention provided that the features of any such combination are not mutually inconsistent.

Further aspects and advantages of the present invention are set forth in the following detailed description and claims, particularly when considered in conjunction with the accompanying drawings in which like parts bear like reference numerals.

DETAILED DESCRIPTION OF THE DRAWINGS

Figure 1:
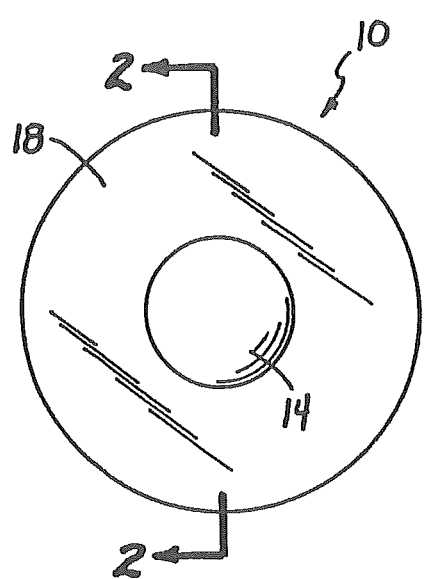
FIG. 1 is a front plan view of an ILC in accordance with the present invention.
Figure 2:
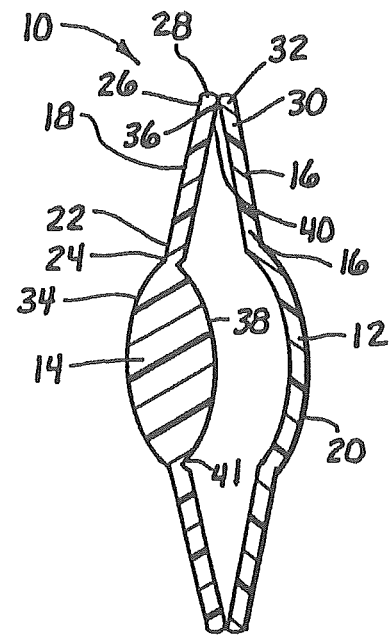
FIG. 2 is a cross-sectional view taken generally along line 2-2 of FIG. 1.

Referring now to FIGS. 1 and 2, an ILC according to the present invention, shown generally at 10, includes a first optic body 12, a second optic body 14, a disc type fixation member 16 and a disc type movement assembly 18.

The first optic body 12 has substantially plano optical power and is adapted to be held in a fixed position, for example, at least partially by the fixation member 16. When the ILC 10 is positioned in a human eye, the posterior surface 20 of first optic body 12 is in contact with the inner posterior wall of the capsular bag of the eye. This positioning of optic body 12 is very effective in reducing or inhibiting endothelial cell growth from the capsular bag onto the first optic body 12. In effect, the positioning of the first optic body 12 against the posterior surface of the capsular bag inhibits or reduce the risk of PCO.

The second optic body 14 includes a distance vision correction power. The movement assembly 18 extends radially outwardly from second optic body 14 and fully circumscribes the second optic body 14. Movement assembly 18 has a proximal end region 22 which is coupled to the second optic body 14 at first optic body periphery 24.

Movement assembly 18 extends radially outwardly to a distal end region 26 including a peripheral zone 28.

Fixation member 16 includes a distal end portion 30 including a peripheral area 32. The movement assembly 18 and fixation member 16 are fused together at the peripheral zone 28 and peripheral area 32. Thus, the entire ILC 10 is a single unitary structure. The first optic body 12 and fixation member 16 can be manufactured separately from second optic body 14 and movement assembly 18 and, after such separate manufacture, the fixation member and movement assembly can be fused together. Alternately, the entire ILC 10 can be manufactured together. Also, if desired, the first optic body 12 and fixation member 16 can be inserted into the eye separately from the second optic body 14 and movement assembly 18. Thus, ILC 10 can comprise a plurality of separate components.

Movement assembly 18 extends outwardly from second optic body 14 sufficiently so that the distal end region 26, and in particular the peripheral zone 28 of the distal end region, is in contact with the inner peripheral wall of the posterior capsular bag when the ILC 10 is implanted in the eye.

As best seen in FIG. 2, when ILC 10 is at rest, the second optic body 14 is positioned vaulted anteriorly relative to the distal end region 26 of movement assembly 18. In other words, the anterior surface 34 of second optic body 14 is anterior of the anterior surface 36 of movement assembly 18 at distal end region 26 and/or the posterior surface 38 of the second optic body 14 is anterior of the posterior surface 40 of the movement assembly at the distal end region.

The first and second optics 12 and 14 may be constructed of rigid biocompatible materials, such as polymethyl methacrylate (PMMA), or flexible, deformable materials, such as silicone polymeric materials, acrylic polymeric materials, hydrogel polymeric materials, and the like, which enable the optics 12 and 14 to be rolled or folded for insertion through a small incision into the eye. Although the first and second optics 12 and 14 as shown are refractive lens bodies, the present ILCs can include at least one diffractive lens body, and such embodiment is included within the scope of the present invention.

As noted previously, first optic body 12 has a substantially plano or zero optical power. Second optic body 14 is prescribed for the wearer of ILC 10 with a baseline or far (distance) diopter power for infinity. Thus, the wearer of ILC 10 is provided with the vision correction power of second optic body 14 with little or no contribution from the first optic body 12.

The fixation member 16 and movement assembly 18, as shown, are integral (unitary) with and circumscribe the first and second optics 12 and 14, respectively. Alternately, fixation member 16 and/or movement assembly 18 can be mechanically or otherwise physically coupled to first optic body 12 and second optic body 14, respectively. Also, the fixation member 16 and/or movement assembly 18 may only partially circumscribe first and second optics 12 and 14, respectively, and such embodiments are included within the scope of the present invention. The fixation member 16 and movement assembly 18 may be constructed from the same or different biocompatible materials as first and second optics 12 and 14, and preferably are made of polymeric materials, such as polypropylene silicone polymeric materials, acrylic polymeric materials, and the like. Movement assembly 18 has sufficient strength and rigidity to be effective to transfer the force from the ciliary muscle of the eye so that the second optic body 14 is movable axially in the eye to effect accommodation.

Movement member 18 includes a region of reduced thickness 41 located at the proximal end region 22. This area of reduced thickness, which completely circumscribes the second optic body 14, acts as a hinge to provide additional flexibility to the movement member 18 to extenuate or amplify the accommodating movement of second optic body 14 in response to the action of the ciliary muscle and zonules.

The fixation member 16 and movement assembly 18 preferably are deformable, in much the same manner as first and second optics 12 and 14 are deformable, to facilitate passing ILC 10 through a small incision into the eye. The material or materials of construction from which fixation member 16 and movement assembly 18 are made are chosen to provide such members with the desired mechanical properties, e.g., strength and/or deformability, to meet the needs of the particular application involved.

The ILC 10 can be inserted into the capsular bag of a mammalian eye using conventional equipment and techniques, for example, after the natural crystalline lens of the eye is removed, such as by using a phacoemulsification technique. The ILC 10 preferably is rolled or folded prior to insertion into the eye, and is inserted through a small incision into the eye and is located in the capsular bag of the eye.

The ILC 10 in the eye is located in a position in the capsular bag so that the posterior surface 20 of first optic body 12 is maintained in contact with the inner posterior wall of the capsular bag. As noted previously, positioning the first optic body 12 in contact with the posterior wall of the capsular bag reduces the risk of or inhibits cell growth from the capsular bag onto the first optic body 12 which, in turn, reduces or inhibits PCO. The ciliary muscle and zonules of the eye provide force sufficient to move axially second optic body 14 sufficiently to provide accommodation to the wearer of ILC 10.

The ILC 10 should be sized to facilitate the movement of the second optic body 14 in response to the action of the ciliary muscle and zonules of the eye in which the ILC is placed.

If the ILC 10 is too large, the ciliary muscle and zonules will be inhibited from effectively contracting/relaxing so that the amount of accommodating movement will be unduly restricted. Of course, if the ILC 10 is too small, the second optic body 14 will be ineffective to focus light on the retina of the eye, may cause glare and/or the movement member may not cooperate with the eye to effect the desired amount of accommodating movement. If the ILC 10 is to be included in an adult human eye, the first and second optics 12 and 14 preferably have diameters in the range of about 3.5 mm to about 7 mm, more preferably in the range of about 5 mm to about 6 mm. The ILC 10 preferably has an overall maximum diameter, with the movement assembly 18 in the unflexed or rest state, in the range of about 8 mm to about 11 mm or about 12 mm.

The present ILC 10 has the ability, in cooperation with the eye, to move the second optic body 14 both posteriorly and anteriorly in the eye, to provide for both distance focus and near focus, respectively. This movement of ILC 10 advantageously occurs in response to action of the ciliary muscle and zonules, which action is substantially similar to that which effects accommodation in an eye having a natural crystalline lens. Thus, the ciliary muscle and zonules require little, if any, retraining to function in accordance with the present invention. The movement member 18, as described herein, preferably is effective to facilitate or even enhance or extenuate the axial movement of the second optic body 14 caused by the action of the ciliary muscle and zonules to provide increased degree of accommodation.

Figure 3:
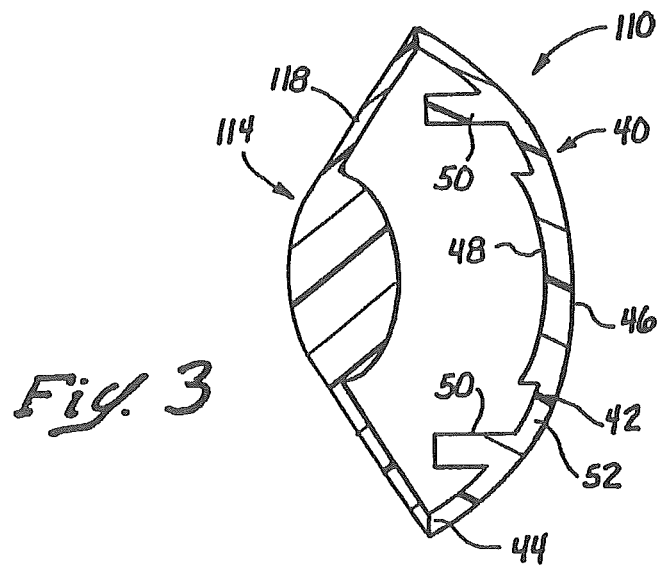
FIG. 3 is a cross-sectional view of an additional ILC in accordance with the present invention.

FIG. 3 illustrates an additional ILC, shown generally at 110, in accordance with the present invention. Except as expressly described herein, ILC 110 is structured and functions similar to ILC 10. Components of ILC 110 which correspond to components of ILC 10 are indicated by the same reference numeral increased by 100.

One primary difference between ILC 110 and ILC 10 relates to the substitution of a posterior lens structure 40 for the first optic body 12 and fixation member 16. Lens structure 40 includes a posterior face 42 which is configured to come in contact with and substantially conform to the inner posterior surface of the capsular bag of the eye in which the ILC 110 is to be placed. Thus, the surface 42 which extends around the peripheral area 44 and across the center region 46 of the lens structure 40 is adapted to come in contact with and substantially conform to the inner posterior wall of the capsular bag. Moreover, the lens structure 40 is adapted to remain in contact with this inner posterior wall of the capsular bag and to be fixed in the eye. This configuration has been found to be very effective in inhibiting cell growth from the eye onto the ILC 110. The anterior surface 48 of lens structure 40 is configured to provide the lens structure with a substantially plano or zero optical power. Second optic body 114 is prescribed for the wearer of ILC 110 with a baseline or distance or far (distance) dioptic power for infinity. Thus, the wearer of ILC 110 is provided with a vision correction power of second optic body 114 with little or no contribution from the lens structure 40.

Alternately, second optic body 114 has a high plus power, for example, plus 30 diopters. The lens structure 40, and in particular the region of the lens structure, defined by the anterior surface 48, which extends substantially across the entire field of vision of the wearer of ILC 110, has a minus vision correction power which is controlled to provide the correction prescription for use in the eye in which the ILC 110 is placed. For example, if this eye requires a plus 15 diopter power, the lens structure 40 has a vision correction power of approximately minus 15 diopters so that the net vision correction power of the combination of lens structure 40 and second optic body 114, is plus 15 diopters.

The lens structure can be made from materials described previously with regard to first optic body 12 and fixation member 16.

One additional feature of lens structure 40 relates to the anteriorly extending projections 50 which extend from the base element 52 of lens structure 40. The number of these projections 50 can range from 2 to about 6 or more. Alternately, a continuous annulus projecting anteriorly can be provided. The purpose of the projections 50 or the continuous annulus is to limit the posterior movement of the second optic body 114 and movement assembly 118. This limitation in the movement provides an additional degree of control of the ILC 110, and prevent a collapse of the ILC 110 and maintains an advantageous degree of separation between second optic body 114 and anterior surface 48 of lens structure 40.

Figure 4:
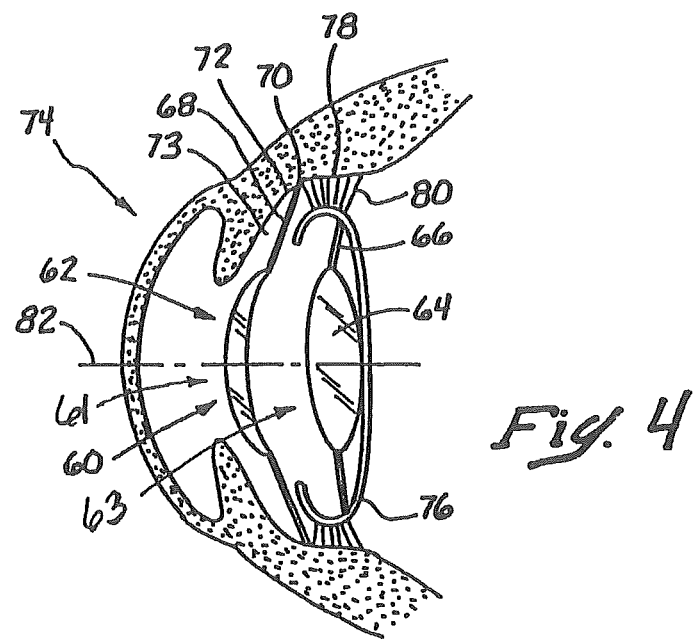
FIG. 4 is a fragmentary sectional view of an eye in which an alternate ILC in accordance with the present invention has been implanted.

FIG. 4 illustrates the use of an alternate ILC in accordance with the present invention. This ILC, shown generally at 60 includes a compensating IOL 61 comprising a first, or compensating, optic body 62, and a primary IOL 63 comprising a second, or primary, optic body 64 and a movement assembly 66. The compensating optic body 62 is coupled to a fixation member 68 which includes a distal end portion 70 in contact with the periphery 72 of the sulcus 73 of eye 74. Fixation member 68 is a disk fixation member which completely circumscribes the compensating optic body 62. However, it should be noted that the disc fixation member 68 can be replaced by two or more filament fixation members or plate fixation members or other types of fixation members, many of which are conventional and well known in the art. Movement assembly 66 is coupled to the primary optic body 64 and completely circumscribes the primary optic body. The primary optic body 64 is located in the capsular bag 76 of eye 74 and is vaulted anteriorly to some extent to enhance accommodating movement of the primary optic body.

The primary optic body 64 has a plus power higher than the power required by the basic prescription of a presbyopic patient. For instance for a patient requiring plus 15 diopters of far vision correction, primary optic body 64 might have a corrective power of plus 30 diopters. The compensating optic body 62 is a negative or minus lens having a minus vision correction power which is controlled to provide the correct prescription for use in eye 74. For the patient described above, the compensating optic body 62 has a vision correction power of approximately minus 15 diopters so that the net vision correction power of the combination of compensating optic body 62 and primary optic body 64 equals the patient's basic prescription of plus 15 diopters. The compensating optic body 62, fixation member 68, primary optic body 64 and movement assembly 66 can be made from materials described previously with regard to the first optic body 12, fixation member 16, second optic body 14 and movement assembly 18, respectively.

The compensating optic body 62 is shown here as a meniscus style optic body; that is, the anterior surface of the optic body is convex and the posterior surface is concave. However, other negative diopter configurations could also be used, such as plano/concave or biconcave. In addition, one or both of the surfaces of the compensating optic body 62 could be multifocal or aspheric to allow for additional accommodation.

In the configuration shown in FIG. 4, the fixation member 68 is in contact with the periphery 72 of the sulcus 73 of the eye 74. This is a relatively durable component of the eye and is effective to support the fixation member 68 in maintaining the compensating optic body 62 in a fixed position.

The movement assembly 66 cooperates with the ciliary muscle 78 and zonules 80 of eye 74 to move the second optic body 64 axially along optical axis 82 of the eye. The amount of axial movement achieved will vary from patient to patient depending on such parameters as capsular bag dimensions. However, the movement should be at least about 0.5 mm, and more preferably, at least about 0.75 mm In a very useful embodiment, the accommodation assembly should allow about 1 mm to about 1.2 mm of movement. With a primary optic body 64 having a corrective power of plus 30 diopters, this amount of movement will be amplified to create an additional add power, or diopter shift, of about 1.75 to about 2.5, or possibly as high as 3.5 diopters. A diopter shift in this range is consistent with the near vision, or add, prescription of a "typical" presbyopic patient.

Figure 5:
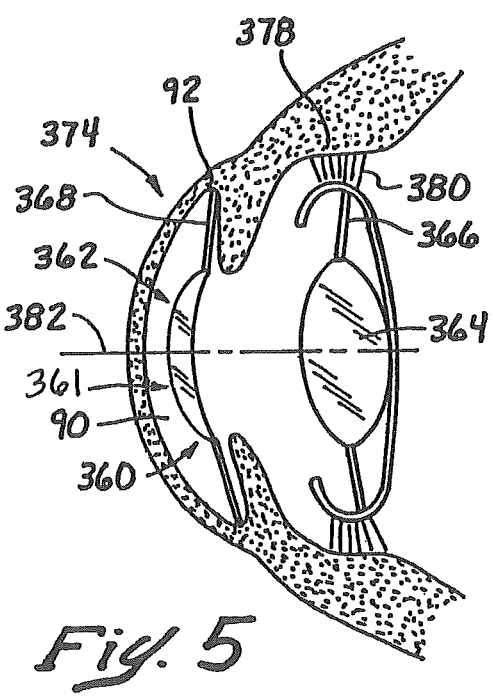
FIG. 5 is a fragmentary sectional view, similar to FIG. 4, in which the compensating optic body of the ILC is implanted in the anterior chamber of the eye.

FIG. 5 illustrates another ILC, shown generally at 360, in accordance with the present invention. Except as expressly described herein, ILC 360 is structured and functions similarly to ILC 60. Components of ILC 360 which correspond to components of ILC 60 are identified by the same reference numeral increased by 300.

One primary difference between ILC 360 and ILC 60 relates to the positioning of compensating optic body 362. Specifically, compensating IOL 361 is located in anterior chamber 90 of eye 374. Fixation member 368 is coupled to the compensating optic body 362 and extends outwardly and comes in contact with the angle 92 of eye 374. The arrangement of compensating optic body 362 and fixation member 368 is such that the compensating optic body is maintained in a substantially stationary position in the anterior chamber 90 of eye 374. The primary optic body 364 is adapted to be moved axially along optical axis 382 of eye 374 by the ciliary muscle 378 and zonules 380 acting on the movement assembly 366.

Figure 7:
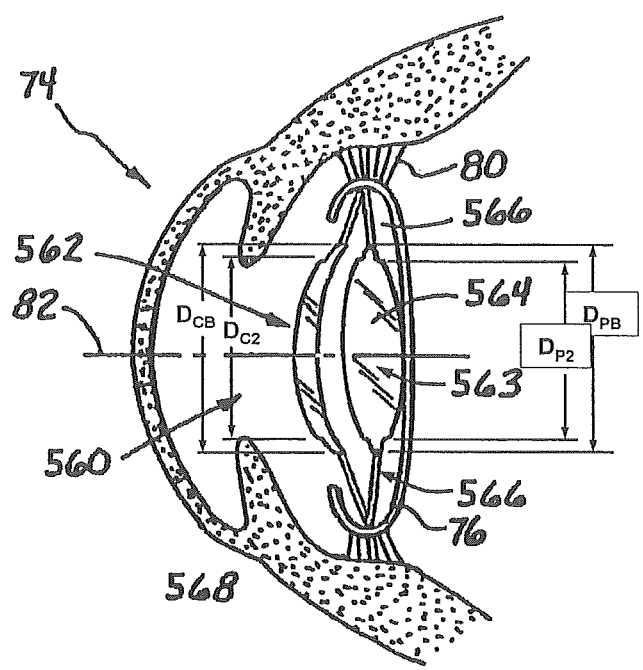
FIG. 7 is a fragmentary sectional view, similar to FIGS. 4 and 5, in which the compensating optic body of the ILC is implanted in the capsular bag of the eye.

Still another embodiment of an ILC according to the present invention is shown in FIG. 7, indicated generally at 560. Except as expressly described herein, ILC 560 is structured and functions similarly to ILC 60. Components of ILC 560 which correspond to components of ILC 60 are identified by the same reference numeral increased by 500.

Again, ILC 560 differs from ILC 60 primarily in the location of the compensating IOL 561, which is located in the capsular bag 76 with the primary optic body 564, rather than in the sulcus or anterior chamber. In this configuration, the compensating optic body 562 would not be truly stationary since the capsular bag 76 itself typically moves about 0.4 mm during accommodation. However, axial movement of the compensating optic body 562 relative the capsular bag 76 can be limited by appropriate design of the fixation member or members 568. Controlling other factors such as material selection, length, width and angulation of the fixation member or members 58 relative the compensating optic body 562 can limit the overall axial movement of the compensating optic body 562 to less than 0.5 mm which, for the purposes of this invention, can be regarded as "substantially fixed."

A preferred method of implanting an ILC will now be discussed. The method is equally effective for the embodiments of FIGS. 5, 6, and 7, but for purposes of illustration will be discussed specifically with reference to FIG. 7.

Initially, the primary IOL 563 is inserted through an incision in the patient's cornea and positioned in the capsular bag 76 using conventional techniques. Preferably, the incision is less than 4 mm in length. If the primary optic body 564 and movement assembly 566 are unitary as illustrated, they are inserted simultaneously. However, it is also possible to implant an independent movement assembly 566 first, and then insert the primary optic body in the movement assembly 566.

After the primary IOL 563 is placed in the capsular bag 76, a measurement is taken to determine the location of the primary optic body 564 relative to the optical axis 82. If desired, refractive measurements may also be made at this time to accurately determine an appropriate prescription for the compensating IOL 561.

If the original incision is still open, the compensating IOL 561 is inserted through the same incision using conventional techniques. If the incision has closed, a new one, preferably also measuring less than 4 mm, is made before insertion. A keratoscope or similar instrument is then used to guide the surgeon in positioning the fixation member or members 568 such that compensating optic body 562 and the primary optic body 564 are axially aligned with the optical axis 82 and one another. If necessary, the primary optic body 564 may also be repositioned at this time.

Alignment of the two optic bodies 562 and 564 is a crucial aspect of this invention, since any decentration of images will be amplified by the high diopter power of the primary optic body 564. Visual confirmation of alignment can be facilitated by providing the compensating optic body 562 with a diameter $D_{CB}$ equal to the diameter $D_{PB}$ of the primary optic body 564.

In addition, the ILC 560 can be made less sensitive to decentration by increasing the diameter of the optic zone, that is the portion of the optic body which has corrective power, in one or both of the IOLs 561 and 563. For instance, while the optic zones of prior art IOLs typically have a diameter in the range of about 3.5 mm to about 7 mm, the diameters of the optic zones $D_{PZ}$ and $D_{CZ}$ in IOLS 561 and 563, respectively, should be in the high end of that range or even higher, i.e. preferably from 5 mm to 8 mm. Even more preferably, at least one of the optic zone diameters $D_{PZ}$ or $D_{CZ}$ should be in the range of about 6.5 mm to about 8 mm. Although, as mentioned previously, the diameters $D_{PB}$ and $D_{CB}$ of the optic bodies 562 and 564 are preferably equal, the diameters $D_{PZ}$ and $D_{CZ}$ of the optic zones need not be.

Another factor influencing centration is the flexibility of fixation member or members 568. Preferably the member or members 568 are sufficiently flexible to allow the surgeon to reposition them as needed during the implantation process, but stiff enough to remain in a substantially fixed axial and radial position once implanted.

Figure 6:
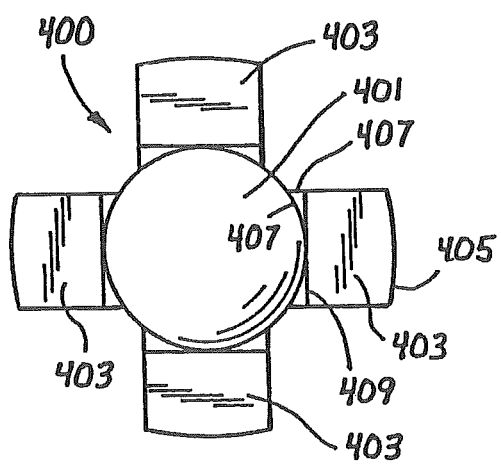
FIG. 6 is a front plan view of an intraocular lens useful in an ILC in accordance with the present invention.

FIG. 6 illustrates a still further embodiment of an intraocular lens in accordance with the present invention. This intraocular lens, shown generally at 400 includes an optic body 401 and four (4) equally spaced apart movement members 403. Each of the movement members 403 includes a distal region 405 and a proximal region 407 which is coupled to the optic body 401. A hinge, for example, a linear hinge, such as a reduced thickness area 409, is located near the proximal end 407 of each of the movement members 403. A linear hinge is particularly advantageous to achieve enhanced, or even substantially maximum theoretical, axial movement.

The IOL 400 can be used in place of the various second optic/movement assembly subcombinations noted above. One distinction between IOL 400 and these other subcombinations is the use of four (4) individual movement members 403 which do not totally circumscribe the optic body 401 relative to the movement assemblies noted previously which fully circumscribe the second optics. It should be noted that the movement assemblies of the present ILCs can have other configurations, for example, which are effective to facilitate or even enhance the movement of the second optics.

While this invention has been described with respect to various specific examples and embodiments, it is to be understood that the invention is not limited thereto and that it can be variously practiced within the scope of the following claims.

What is claimed:

1. An accommodating intraocular lens having an optical axis, comprising:
    an anterior optic having positive refractive power;
    a posterior optic having negative refractive power;
    an anterior biasing element comprised of an anterior distal end portion and a proximal portion, wherein the proximal portion is comprised of an area of reduced thickness which completely circumscribes the anterior optic and is configured to provide additional flexibility to the anterior biasing element; and
    a posterior biasing element comprised of a posterior distal end portion;
    wherein the anterior distal end portion and the posterior distal end portion intersect at a peripheral zone surrounding a portion of the optics as viewed from the anterior or posterior side;
    wherein the peripheral zone has an outer surface for engaging a capsular bag, and wherein at least one corner is formed at the outer surface of the peripheral zone by the intersection of the anterior distal end portion and the posterior distal end portion.

2. The accommodating intraocular lens of claim 1, wherein a radially inner surface of the anterior and posterior biasing elements is concave at an equatorial plane disposed between the anterior and the posterior optics such that the accommodating intraocular lens is configured to engage the capsular bag at the equatorial plane of the accommodating intraocular lens.

3. The accommodating intraocular lens of claim 1, wherein the anterior biasing element extends radially outwardly from the anterior optic and defines a continuous periphery around the anterior optic.

4. The accommodating intraocular lens of claim 1, wherein the anterior biasing element extends generally linearly from the anterior optic to the peripheral zone and the posterior biasing element extends generally linearly from the posterior optic to the peripheral zone.

5. The accommodating intraocular lens of claim 1, wherein the anterior optic and the anterior biasing element are separate components from the posterior optic and the posterior biasing element.

\* \* \* \* \*